(12) United States Patent
Blake (10) Patent No.: US 6,298,853 B1
(45) Date of Patent: Oct. 9, 2001

(54) BILATERALLY SYMMETRIC ABBREVIATED CONDOM

(76) Inventor: Rory P. Blake, 3216 Chaucer Dr., Charlotte, NC (US) 28210

( * ) Notice: Subject to any disclaimer, the term of this patent is extended or adjusted under 35 U.S.C. 154(b) by 0 days.

(21) Appl. No.: 09/517,735

(22) Filed: Mar. 3, 2000

(51) Int. Cl.[7] ....................................................... A61F 6/04
(52) U.S. Cl. ........................................... 128/844; 128/918
(58) Field of Search ..................................... 128/842, 844, 128/918; 604/347–353

(56) References Cited

U.S. PATENT DOCUMENTS

| | | | | |
|---|---|---|---|---|
| 4,821,742 | * | 4/1989 | Phelps | 128/842 |
| 4,869,269 | * | 9/1989 | Sharkan | 128/844 |
| 5,421,350 | * | 6/1995 | Friedman | 128/918 |
| 5,579,784 | * | 12/1996 | Harari | 128/844 |
| 5,638,829 | * | 6/1997 | Najor | 128/844 |
| 5,741,511 | * | 4/1998 | Lee | 128/842 |
| 5,979,447 | * | 11/1999 | Al-Falahe | 128/844 |

* cited by examiner

Primary Examiner—Michael A. Brown

(74) Attorney, Agent, or Firm—Peter Gibson (57) ABSTRACT

Securement of a condom to the glans penis is facilitated by a pair of bilaterally symmetric areas provided for the lobes of the glans penis. It is recommended that the bilateral convex shape of the two lobes of the glans penis be adhered to by a close fitting shape molded into the condom which will resist accidental upward displacement. A viscous layer upon the interior surface enhances the suction characteristics in providing a greater cohesion coefficient between the condom and the skin contacted. A plurality of vacuum cups molded into the interior surface of the condom is also suggested. An expansible seminal fluid reservoir is provided, preferably located between the lobes of the glans are upon the tip of the condom. The resistance to accidental upward displacement provided by the suction areas adhered to the glans permit the condom to be severely abbreviated in length which allows greater sensitivity and a stronger condom more resistant to tearing during use than a conventional full length latex condom. Correct positioning may be facilitated by a reversible margin proximate the open rear edge which fits into the sulcus behind the corona. A circumferential adhesive layer is recommended to obtain a seal against fluid transmission and the use of a thin film backing upon the same further facilitates positioning of the condom. Manufacture by injection molding is suggested as is use of a plastic which may be transparent.

20 Claims, 4 Drawing Sheets

BILATERALLY SYMMETRIC ABBREVIATED CONDOM

BACKGROUND OF THE INVENTION

1. Field of the Invention

The general field of the present invention relates to condoms, i.e. prophylactic sheaths, and more particularly to condoms which are of abbreviated length which substantially cover the glans penis only during use.

General Background

Condoms have traditionally served as a means of prophylaxis against conception. More recently, with the development of birth control pills and the increase in contagion of various sexually transmitted diseases, (STDs), condoms have become valued more, perhaps, as a means of prophylaxis against transmission of SIDs than against conception. Several aspects regarding the use of condoms as opposed to other forms of preventing conception are recognized. Condoms are known to break during use and other forms of preventing conception, primarily birth control pills, are generally considered to be at least as effective as a condom for preventing conception.

The woman, moreover, possesses an assurance in knowing she is relatively safe from pregnancy if she is taking birth control pills regularly. A condom may break during use and while the man may readily discern this condition the woman cannot. A man might ignore the breakage or be truly unaware of the same and in either case the woman is typically without recourse to remedy the situation in which she has the more direct interest. The presence of a conventional full length latex condom essentially is not noticed by a female during intercourse but the same drastically reduces the sensitivity of the penis and the pleasure derived from the same activity for males who consequently frequently dislike wearing condoms for this reason. It is considered that the male aversion to wearing of a conventional full length latex condom was and is still a major factor in the adoption of alternative birth control measures by women.

In addition to birth control pills, interuterine devices, (IUDs), diaphragms and spermicidal jelly have been widely popular as alternatives to condoms for the prevention of unwanted pregnancies. The popularity of these measures is considered in view of the disadvantages associated with each. Birth control pills alter the body's chemistry and although the levels of estrogen and progestogen utilized has been decreased over the last several decades of use the fact remains that side effects attend regular and particularly regular and prolonged use of birth control pills. RIDs have been associated with serious medical problems for various reasons and many women generally find the implantation of the devices to be objectionable and the presence of the devices to be a marked source of discomfort. The use of diaphragms and spermicidal jelly poses a considerable inconvenience upon the woman as insertion is often difficult and the required presence of the device for many hours after intercourse is often uncomfortable. However, despite all these inconveniences, all three methods have been and are still quite popular as an alternative to the use of conventional condoms which pose neither inconvenience nor discomfort nor threat of physical side effects to the woman other than the reliance upon the willing cooperation of the male including detection of the breaking and prompt replacement of a broken condom during use.

In essence it is considered that, for the purposes of preventing unwanted pregnancy, many forms of contraception are preferred as alternatives to the use of a conventional full length latex condom by women despite the discomfort and risks associated with these alternatives because men dislike wearing conventional full length latex condoms and can not be reliably expected to use the same in a responsible manner simply because of the adverse affect upon the sensitivity of the penis imposed by the wearing of this prophylactic sheath. Most recently, approval has been granted for the marketing of a "morning after" birth control pill which will enable women to prevent contraception hours after coitus, hence practically removing any inhibition against having intercourse imposed by the adoption of a prophylaxis against an unwanted pregnancy.

However, there is no known alternative to a prophylactic device worn by the male for the prevention of infection by STDs during coitus. A conventional full length latex condom is widely recognized as the only effective means of avoiding STD contagion during coitus and is generally considered effective in protecting the male as well as the female from contacting a STD from the other during intercourse. The transmission of a disease from a male to a female during coitus is considered mainly to be associated with transfer of seminal fluid. More specifically, it is the absorption of the seminal fluid by mucous membranes such as that which line the vagina, which is considered to result in the sexual transmission of a disease from a male to a female during coitus. A regards the reverse process, i.e. the transmission of disease from the female to the male during coitus, it is considered that for a healthy, epidermally unbroken, penis only the urethra provides a mucous membrane lining which is susceptible to infection but without a condom this avenue of infection is quite adequate for the acquisition of a STD by the male.

In short, it is recognized that men dislike wearing conventional full length condoms because of the loss of sensitivity which results and if the avoidance of pregnancy is the only concern there are other contraceptive alternatives to the use of a condom by the man which the woman may adopt, however, only a condom is considered effective in preventing the transmission of disease during coitus. Therefore, despite the many various advances in contraceptives over the last several decades touched upon above, relatively recent condom development, as evidenced by the number of U.S. Patents issued annually for the same, accelerated markedly in response to the increase in SIDs during the last fifteen years in the United States. This recent development, as discussed below, includes consideration of an abbreviated condom which would not greatly diminish sensitivity and hence would be less objectionable to use by the male. As discussed at some length above, the loss of sensitivity imposed by wearing of a conventional full length latex condom is considered central to the common male aversion to proper use of the same and this aversion is considered to be the main reason the risk of acquiring a STD is tolerated by both men and women.

2. Discussion of the Prior Art

U.S. Pat. No. 2,703,574 issued to A Hirschfeld on Mar. 8, 1955 discloses a 'Rubber Sanitary Device' or abbreviated condom intended to enclose the glans penis and be held in place by a bottom thickened ring or band intended to seal the device "in engagement with the posterior annular portion of the glans" (Col. 1, Lines 60–62); which is bulb shaped and radially symmetrical about a central vertical axis, "an intermediate section of said receptacle portion being circular in cross section" (Column 2, Lines 28–29).

DT 25 19 357 issued to A. Kopelowicz on Nov. 11, 1976 for an 'Elastic Cap Contraceptive Sheath' discloses an abbreviated condom for enclosing the glans penis with a tip located reservoir possessing "concertina folds" (English Abstract) held in place by a bottom adhesive band which folds over after location of the radially symmetric device.

U.S. Pat. No. 4,820,290 issued to James H. Yahr on Apr. 11, 1989 for a 'Prophylactic Device' discloses an abbreviated condom of radially symmetric dimensions intended to enclose the glans penis and being held in place by a thickened band "to be positioned in the coronal sulcus to prevent leakage of fluids collected in the hood" (Abstract) which is at least thrice as wide as it is thick to prevent rolling.

U.S. Pat. No. 4,821,742 issued to John Y. Phelps, III on Apr. 18, 1989 for a 'Contraceptive Device' discloses an abbreviated condom intended to fit upon the glans penis above the corona and held in place by adhesive interrupted in areas central and extending radially downward from the top of the device which is "of substantially semi-spherical shape" except for a tip located reservoir.

U.S. Pat. No. 4,869,269 issued Sep. 26, 1989 to Arnold L. Sharkan for a 'Contraceptive Device: Micro-Condom' discloses use of adhesive to form a seal with the glans penis which "eliminates the need for the roll-down hood" and whereby "the breakage problem" may be "solved with thicker material" (Abstract) and which further has a single indenture 15 "in the frusto-conical portion 14 to correspond approximately the indenture in the underside of the" glans penis (Column 3, Lines 22–24).

CA 2034764-A issued to Richard Sauve on Jul. 24, 1992 for a 'Condom For Protection During Sex' discloses an abbreviated condom intended to enclose the glans penis, and being held in place by a thickened band below the glans having a expansible receptacle on the top folded flat during use prior to ejaculation.

U.S. Pat. No. 5,421,350 issued to Leah Friedman on Jun. 6, 1995 for a 'Condom Having Adhesive Means' discloses an abbreviated condom which has an angled open end but an otherwise radially symmetric structure which it is secured by both a bottom annular reinforcement or rim and adhesive contacting the glans with a tip reservoir for seminal fluid.

U.S. Pat. No. 5,458,114 issued Oct. 17, 1995 to Jan E. Herr for a 'Contraceptive Penile Cap' discloses a bowl shaped structure held onto the glans with "medical grade adhesive" possessing a "collapsed bladder contained within a protective retaining structure" for the semen whereby the "sensitive corona of the glans is left exposed" (Abstract).

U.S. Pat. No. 5,823,191 issued Oct. 20, 1998 to Gill-Ho Cho discloses a radially symmetric 'Condom' possessing a "supporting portion" rearward of the corona which is thicker than the forward "condom sack" about the glans "compressing the penis only enough to prevent the condom from slipping out," without "disturbing the blood circulation in the spongeness structure of the glans" and facilitating "reuse" (Abstract).

Statement of Need

The prior art discussed above demonstrates a variety of abbreviated condoms fitting either around the glans or attached with adhesive thereto. In particular, it is noted that a number of aspects may be recognized in the attempt to achieve satisfactory attachment to the glans penis only have been disclosed in the prior art: use of a band below the corona or ridge of the glans; use of adhesive; use of an angled rim below the corona; use of a thicker supporting sheath below the corona; use of collapsible reservoirs; and use of a single indenture in what is otherwise a frusto-conical shape. In all cases except for the angled rim and the single indenture the condom is symmetrically radial about a central vertical axis.

As essentially demonstrated by the variety of abbreviated condoms developed over the last forty-five years chronicled above it is considered that the central problem of obtaining a secure attachment of such a device with a sufficient reservoir which possesses effective resistance to accidental displacement as well as breakage has not been solved and that therefore a need still exists for an abbreviated condom which will reliably protect against an exchange of seminal fluid while leaving most of the penis exposed in order to provide greater sensitivity and hence greater use.

In particular, it is considered that the prior art fails to disclose a structure which is shaped to conform to the bilaterally symmetric structure of the glans which possesses two convex lobes on the underside or ventral half of the head of the penis. The pertinent prior art is characterized generally by use of a radially symmetric structure which assumes a radially symmetric glans penis which is inaccurate; the corona is angled as seen from either side and the ventral glans is characterized by a central cleft between two bilaterally symmetric convex shaped lobes. Because a bilateral shape construction which would conform to the lobes of the glans is unknown in the prior art and because it is considered that the same will ensure an effective seal against leakage of seminal fluid in attachment to the glans penis a need for the same is recognized.

SUMMARY OF THE INVENTION

Objects of the Invention

The encompassing object of the principles relating to the present invention is the provision of a condom of abbreviated length possessing a structure that conforms anatomically to the glans penis, including a pair of bilateral outwardly convex ventral portions which conform to the two lobes of the glans penis, thereby enabling effective securement of the condom and sealing the same against fluid transmission.

A first auxiliary object of the principles relating to the present invention is the provision of a condom of abbreviated length which possesses a structure which, under a force acting to displace the condom upward with respect to the penis, exerts a negative pressure differential, i.e. suction, upon the glans penis.

A first ancillary objective of the principles relating to the present invention is the provision of a condom of abbreviated length which a possesses a structure which includes a pair of bilateral outwardly convex ventral portions which, in conformance with the two lobes of the glans penis and under a force acting to displace the condom upward with respect to the penis, exerts a negative pressure differential, i.e. suction, upon the glans penis.

A second ancillary objective of the principles relating to the present invention is the provision of a condom of abbreviated length which a possesses a structure which includes a plurality of vacuum cups molded into the interior surface which, under a force acting to displace the condom upward with respect to the penis, exerts a negative pressure differential, i.e. suction, upon the glans penis.

A second auxiliary object of the principles relating to the present invention is the provision of a condom of abbreviated length which possesses a circumferential viscous layer disposed upon an interior surface including a pair of bilateral outwardly convex ventral portions which conform to the pair of lobes of the glans in order to achieve a continuous seal about the circumference of the glans penis.

A third auxiliary object of the principles relating to the present invention is the provision of a condom of abbreviated length which possesses a circumferential adhesive layer disposed upon an interior surface whereby a continuous adhesive seal may be obtained.

A fourth auxiliary object of the principles relating to the present invention is the provision of a condom of abbreviated length which possesses a structure that conforms anatomically to the glans penis in which retention of seminal fluid is facilitated by an expansible reservoir.

A third ancillary objective of the principles relating to the present invention is the provision of a condom of abbreviated length which possesses a structure that conforms anatomically to the glans penis in which retention of seminal fluid is facilitated by an expansible reservoir located at the tip.

A fourth ancillary objective of the principles relating to the present invention is the provision of a condom of abbreviated length which possesses a structure that conforms anatomically to the glans penis in which retention of seminal fluid is facilitated by an expansible reservoir located between a pair of bilateral outwardly convex ventral portions which conform anatomically to the two lobes of the glans penis.

A fifth ancillary objective of the principles relating to the present invention is the provision of a condom of abbreviated length which possesses a structure that conforms anatomically to the glans penis which is constructed of a thin film of substantially equal thickness facilitating manufacture by molding.

Principles Relating to the Present Invention

Achieving anatomical conformance with the glans penis is considered fundamental to the principles relating to the present invention. Taking the opening of the urethra at the tip of the penis as the most forward point with the penis disposed horizontally it is first observed that the entire penis is bilaterally symmetric about a central vertical plane. The glans penis is observed to have, in this orientation, a large upper or dorsal portion extending rearwardly and angled upwardly from the lower or ventral and forward bilateral lobes between which there is a cleft opening outward upon the ventral shaft of the penis.

If this bilateral aspect to the glans penis is ignored, and radial symmetry about a central axis is assumed in the structure of an abbreviated condom, the gap between the lobes is considered to present a problem with regard to sealing against fluid transmission and securement of the condom against accidental dislodgement. The pronounced rearward dorsal ridge of the corona of the glans penis has been recognized as providing a structure behind which a band located in the sulcus will readily provide resistance to upward displacement and the assumption of radial symmetry in the ventral portion of the glans penis imagines a continuous circumference by the corona which would allow a band located in the sulcus to also form an effective seal against fluid transmission.

The corona however, which possesses such a pronounced unitary ridge along the dorsal rear edge of the glans penis, ventrally and forwardly melds into the bilaterally symmetric convex forms of the two lobes of the glans between which a cleft widens rearwardly in a concave V shape. It is considered desirable to provide an abbreviated condom which recognizes this anatomy and which possesses a structure which will conform to the bilaterally symmetric convex forms of the two lobes in the obtainment of a circumferential seal of the glans penis. Without anatomical conformance to the entire glans, including the forward and ventral lobes, both securement of an abbreviated condom to and sealing of the condom about the glans penis is considered problematic.

With anatomical conformance to the entire glans, including the lobes, an abbreviated condom in accordance with the principles relating to the present invention readily obtains a circumferential seal of the glans penis and resistance to accidental displacement forward. With a viscous liquid disposed on the interior surface of the condom an adhesive force between the condom and the penis is effected which resists by the resultant negative pressure differential, i.e. suction, displacement of the condom from the penis.

In addition to the suction resultant from the close contact between penis and condom and viscous layer therebetween it is also suggested that a plurality of vacuum cups be molded into the interior surface of the condom in a circumferential pattern including the bilateral convex ventral portions shaped to conform to the two forward and ventral lobes of the glans penis. It is also suggested that a layer of adhesive in a similar pattern be disposed upon the interior surface of the abbreviated condom in accordance with the principles relating to the present invention.

An expansible reservoir is considered prudent which is preferably located either at the tip of the condom, in front of the urethra opening, or between the two ventral lobes of the glans penis. In the former case a circumferential seal about the glans penis only will enable an effective seal against transmission of fluids. In the latter case a circumferential seal behind the reservoir and well behind the ventral lobes of the glans penis is indicated. In either case it is recommended that the circumferential seal be located off of the area immediately between the forward ventral lobes as this area is considered to be characterized by particularly soft, flaccid, tissue further lacking in smoothness and hence unsuited, by both reasons, to adhesion.

It is considered that in order to achieve a satisfactorily accurate anatomical conformance with the bilaterally symmetric glans penis, particularly with regard to the two bilateral forward and ventral lobes of the glans, molding of an abbreviated condom in accordance with the principles relating to the present invention with a mold which is bilaterally symmetric but not radially symmetric is indicated. While material of sufficient flexibility such as latex and sufficiently thin wall thickness further equipped with a viscous interior layer, which attributes are considered to characterize a conventional fall length, condom, will largely conform anatomically to the entire penis including the bilaterally symmetric lobes of the glans, one of the larger problems attributed to conventional condoms is tearing of the same during use and use of thicker material is considered the only practical solution to this problem.

It is hence suggested that an abbreviated condom in accordance with the principles relating to the present invention possess a wall thickness which is substantially greater than that possessed of a conventional, full length condom, and that the wall thickness be substantially equal in order to facilitate molding. It is also considered that materials other than latex may be utilized and suggested that a relatively flexible polymer material, which is still relatively stiff in comparison with latex, be utilized in order to obtain the non-radially symmetric shape required and to provide superior resistance to tearing during use. It is further suggested that a substantially transparent polymer be utilized for aesthetic purposes. And if a circumferential adhesive layer is utilized it is suggested that a thin film backing for this adhesive layer be provided, preferably with a tab to facilitate removal after proper location.

DETAILED DISCUSSION OF THE PREFERRED EMBODIMENTS

An abbreviated condom 10 in accordance with the principles relating to the present invention as depicted in FIGS. 1–8 possesses an open rear edge 11, two bilaterally symmetric convex portions 12, a forward tip 13, and a seminal fluid reservoir 14, 24. This abbreviated condom 10 is intended to be fitted upon the glans penis 15 as shown in FIGS. 1–6 encompassing at least that portion of the corona 16 which melds into each bilaterally symmetric lobe 25 with which each bilaterally symmetric convex portion 12 conforms anatomically to achieve an adhesive contact.

Figure 8:
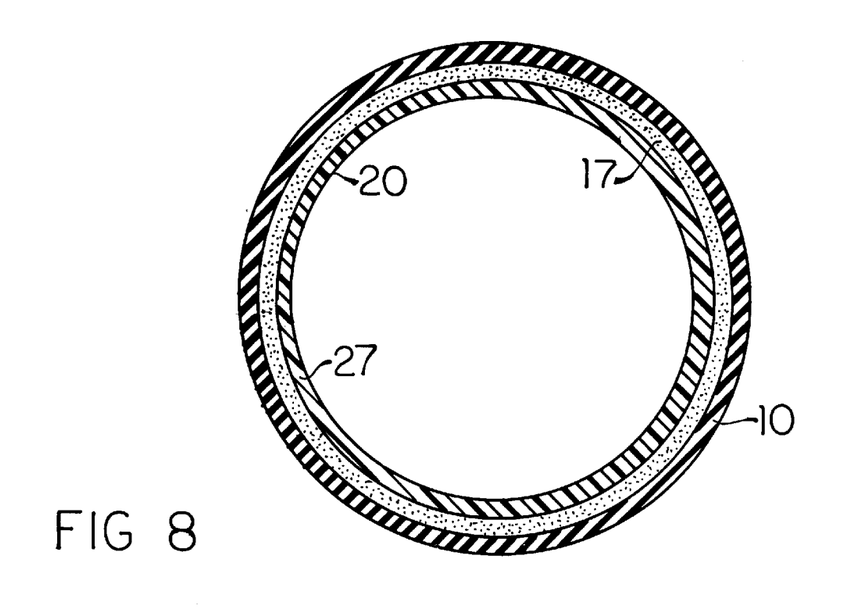
FIG. 8 is a cross sectional view of proximate the open rear edge of an preferred embodiment of the principles relating to the present invention showing a circumferential adhesive layer and backing for the same.

A preferred embodiment of the principles relating to the present invention, as depicted in FIGS. 1–4, may leave the rear dorsal edge of the corona 16 exposed along with a rear dorsal portion of the glans penis 15 while encompassing the bilaterally symmetric lobes 25 which are anatomically conformed to by the bilaterally symmetric convex portions 12 and further may have a seminal fluid reservoir 14 located therebetween which is preferably fed with an interiorly open, externally raised, channel 23 facilitating the flow of seminal fluid from the urethra opening behind the forward tip 13 of the abbreviated condom 10. It is emphasized that many features are independent of each other and in this case the rear dorsal edge of the corona 16 may be further encompassed still using a circumferential adhesive layer 17 proximate the open rear edge 11 of the abbreviated condom 10 which is seen as an increased thickness in FIGS. 1–4 which adhesive layer 17 is further preferably covered interiorly, as depicted in FIG. 8, with a thin film backing 27.

Figure 1:
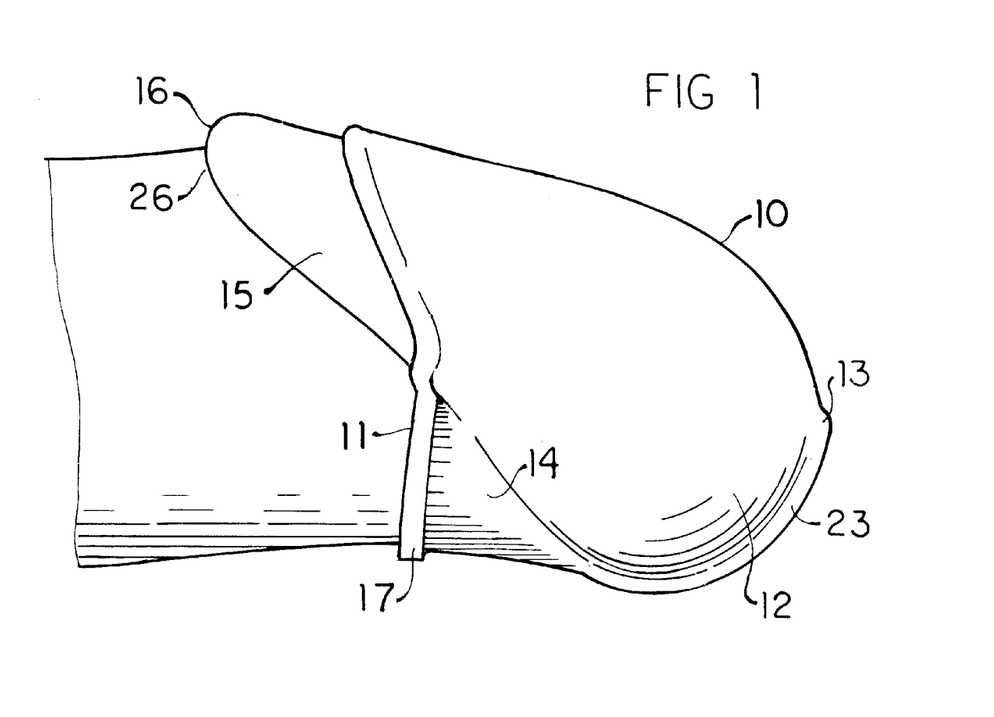
FIG. 1 is a plain elevational view taken from a side of a preferred embodiment of the principles relating to the present invention fitted upon a penis for use.
Figure 2:
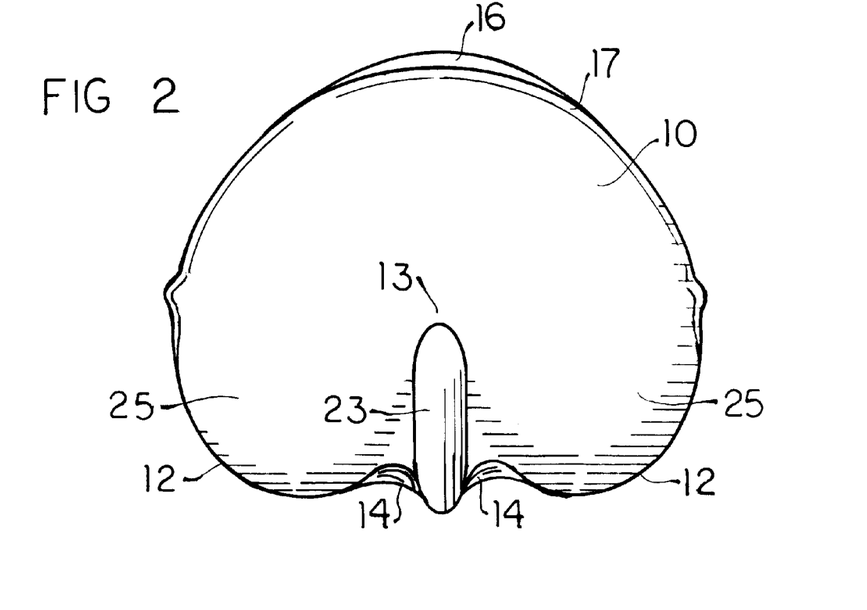
FIG. 2 is a plain elevational view taken from the front of the preferred embodiment of the principles relating to the present invention shown in FIG. 1.
Figure 3:
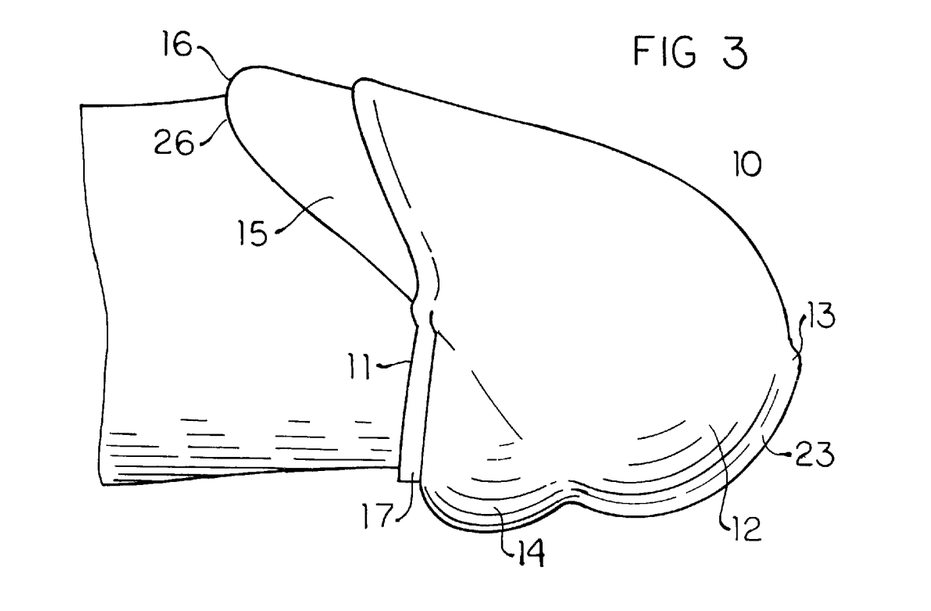
FIG. 3 is a plain elevational view taken from a side of the preferred embodiment of the principles relating to the present invention shown in FIG. 1 after use.
Figure 4:
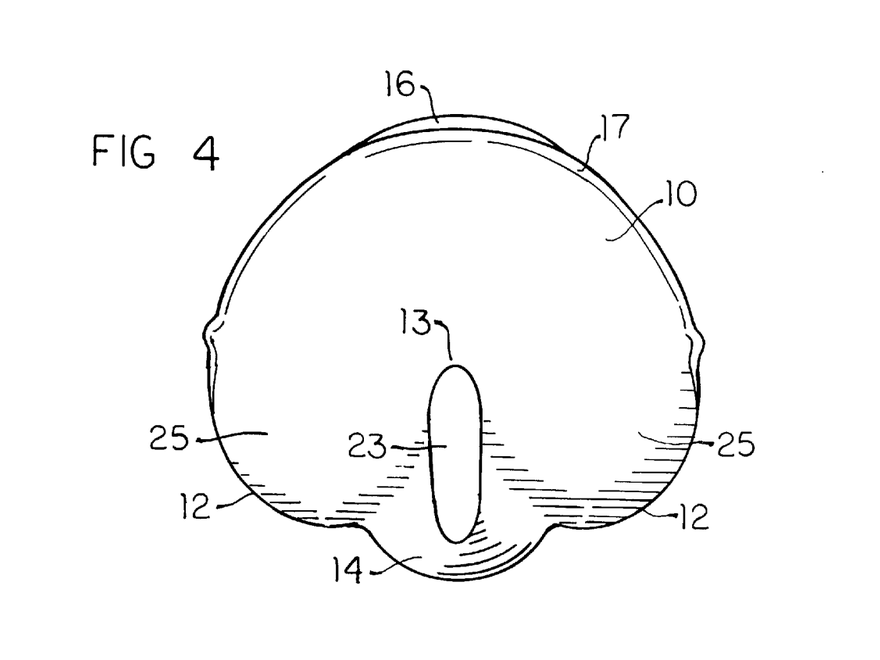
FIG. 4 is a plain elevational view taken from the front of the preferred embodiment of the principles relating to the present invention shown in FIG. 1 after use.

As most clearly seen in FIG. 1, the expansible reservoir 14, located between the two bilaterally symmetric convex portions 12, is characterized by a relatively thin wall thickness which facilitates the expansion clearly seen in FIGS. 3 & 4 in retention of seminal fluid resulting from ejaculation. The area immediately behind the cleft between the two lobes 25 of the glans penis 15, as mentioned previously, is characterized by relatively soft, flaccid, tissue for which reason adhesion with an adhesive layer 17 is undesirable.

Figure 7:
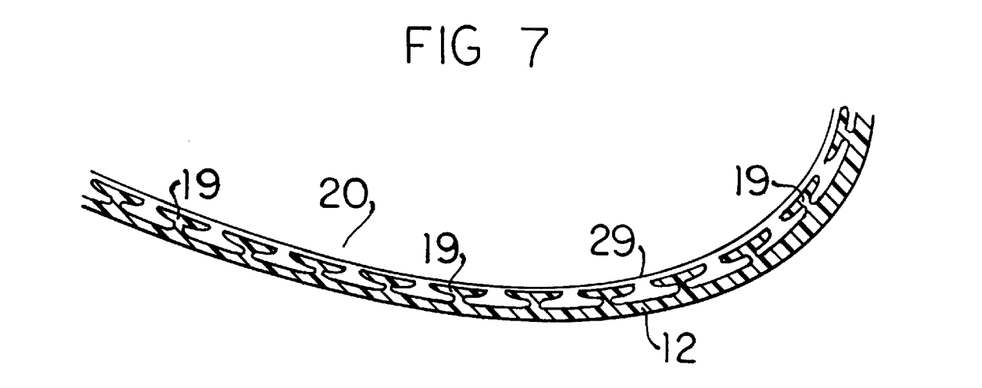
FIG. 7 is a cross sectional view of a bilaterally symmetric convex portion of an preferred embodiment of the principles relating to the present invention showing molded vacuum cups and a viscous layer.

However, the adhesion resulting from the cohesion of the wall of the abbreviated condom 10 to the skin obtained with a viscous layer 29, depicted in FIG. 7, is considered to be comfortable and to present no impediment to expansion of the reservoir 14 by the seminal fluid which is itself a highly viscous fluid. Hence while the adhesion effected by the circumferential adhesive layer 17 is a seal against fluid transmission the adhesion resulting from cohesion of membrane to skin through a viscous layer 29 is not an impediment to the positive interior pressure of the ejaculation though resistance from the negative pressure differential resulting from displacement of the membrane relative to the skin will result. Therefore the use of a viscous layer 29 upon the entire interior surface 20 of the abbreviated condom 10, including that in the area of the reservoir 14, is quite practical.

Figure 5:
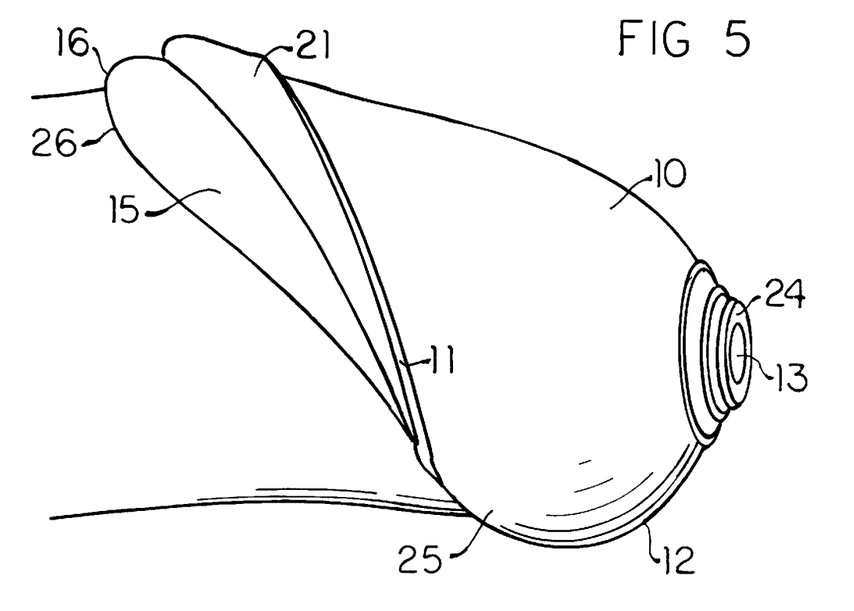
FIG. 5 is a plain elevational view taken from a side of a preferred embodiment of the principles relating to the present invention fitted upon a penis prior to use.
Figure 6:
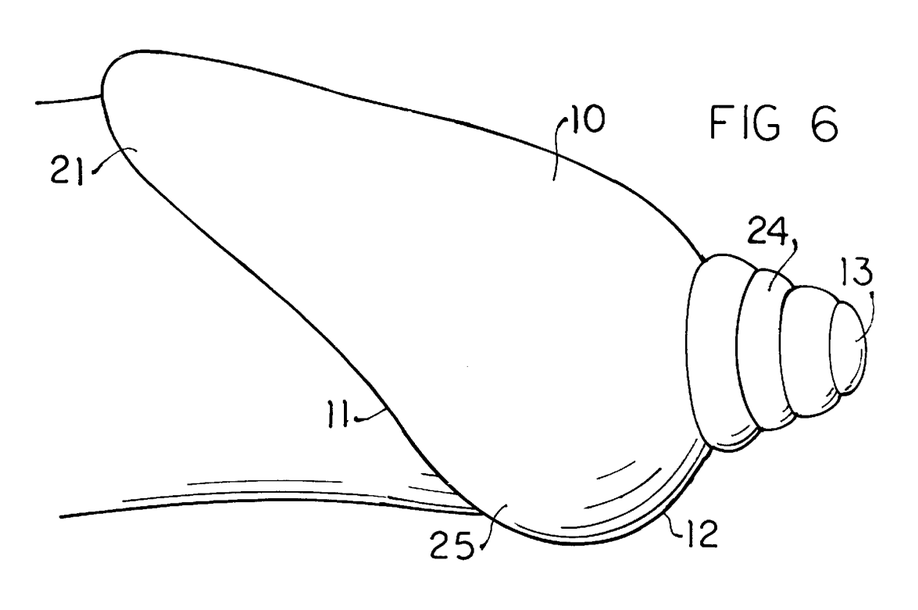
FIG. 6 is a plain elevational view taken from a side of the preferred embodiment of the principles relating to the present invention shown in FIG. 5 after use.

In contrast to the embodiment depicted in FIGS. 1–4 the abbreviated condom 10 depicted in FIGS. 5–6 possesses an accordion type reservoir 24 located at the forward tip 13 which, as seen in FIG. 5, is relatively flat prior ejaculation and, as seen in FIG. 6, expands readily in accommodation of the same. The abbreviated condom 10 depicted in FIGS. 5–6 also utilizes a reversible margin 21 proximate the open rear edge 11 which, as seen in FIG. 5, is intended to be folded forward about the adjacent exterior surface of the abbreviated condom 10 prior to use and flipped rearward behind the corona 16 into the sulcus 26 in fitting upon the glans penis 15 for use, as seen in FIG. 6. In this case also it will be noticed that the abbreviated condom 10 fitted upon the glans penis 15 for use encompasses the entire corona 16 and the positioning of the reversible margin 21 in the sulcus 26 achieves a resistance to accidental forward displacement of the abbreviated condom 10. This, in combination with the suction obtained by the conformance of the bilaterally symmetric convex portions 12 with the lobes 25 of the glans penis 15 and location of the accordion type reservoir 24 at the tip is considered sufficient to prevent fluid transmission without the use of a circumferential adhesive layer 17 which, as mentioned previously, preferably avoids contact with the flaccid area immediately behind the cleft between the lobes 25 of the glans penis 15.

It is recommended particularly in this case, where it is important to obtain a seal about the glans penis 15 without use of a circumferential adhesive layer 17, that a plurality of small vacuum cups 19 be molded into the interior surface 20 of the abbreviated condom 10, as depicted in FIG. 7, particularly in the bilaterally symmetric convex portions 15 which conform to the two bilaterally symmetric lobes 25 of the glans penis 15, in order to obtain an effective seal against fluid transmission forward of the area immediately behind the cleft between the lobes 25. The adhesion of the vacuum cups 19 to the skin of the glans penis 15 resists both accidental displacement forward and expansion by the seminal fluid since the latter is external to the interior of the each adhered vacuum cup 19.

It is also noted that the accordion style reservoir 24 is considered to be very readily expansible in accommodation of seminal fluid resulting from ejaculation which, in combination with the location of the same immediately in front of the opening of the urethra, ensures that the seminal fluid will be retained. With regard to transmission of fluids from outside to inside the abbreviated condom 10 it is considered that the reversible margin 21 positioned in the sulcus 26 is a fairly effective barrier if not a seal and while the adhesion of the interior surface 20 of the abbreviated condom 10 provided by a circumferential band of vacuum cups 19 about the glans penis 15 is also not proof against fluid transmission alone, the two together are considered to comprise an effective seal against transmission of fluid from without.

The transmission of fluids either way is of concern with regard to the transmission of sexually transmitted diseases (STDs). While the retention of seminal fluid is of obvious necessity in preventing undesired impregnation as well as for preventing the transmission of STDs it is also desirable to prevent the less obvious avenue of fluid transmission from outside through the opening of the urethra whereby STDs may be transmitted in the reverse manner. It is considered less likely for fluid transmission to occur in this reverse manner so long as the opening of the urethra is covered and it is also recalled that one of the fundamental failures of conventional condoms has been considered to be tearing during use.

In address of this problem it has been noted that use of thicker material is considered to be the only sure solution and that in a conventional, full length, condom a thicker wall is undesirable because of the loss of sensitivity resulting therefrom which is in addition to higher material costs for the manufacturer. One of the principal advantages expected with an abbreviated condom is greater resistance to tearing obtained with use of thicker material which is essentially enabled by the greater sensitivity resultant from exposing most of the shaft of the penis. A conventional, full length, condom, is typically of a uniform wall thickness being the result of a dip molding operation in latex. This method of manufacture is essentially restricted to a substantially uniform wall thickness and is further characterized by use of radially symmetric molds of substantially constant diameter with a slight taper from front to rear which facilitates both removal from the mold and fitting upon an erect penis.

If no substantial variation in wall thickness is desired it is considered quite feasible to obtain a non-radially symmetric shape with a dip mold including the bilaterally symmetric a convex portions 12 characterizing an embodiment in accordance with the principles relating to the present invention. If a thickened band or reversible margin 21 proximate the open rear end 11 of the abbreviated condom 10 is desired, or an expansible reservoir 14 of relatively thin wall thickness, then it is suggested that an injection or other closed type molding be utilized. Use of an accordion type reservoir 24 such as that depicted in FIGS. 5 & 6 is considered to clearly dictate injection or other closed mold type of molding which process further suggests use of a material different than latex.

A relatively flexible polymer, while still being relatively stiff in comparison with latex, is considered appropriate for manufacture of an abbreviated condom 10 in accordance with the principles relating to the present invention. The very short length in comparison with a conventional, full length, condom enables a smaller and hence less expensive mold as well as production upon a smaller and less expensive injection molding machine. And the specific shape required of the bilaterally symmetric convex portions 12 is considered to be suitable to manufacture by injection molding and the additional stiffness, in comparison with latex, of a relatively flexible polymer product is also considered suitable as regards function. A transparent polymer is further suggested for aesthetic purposes.

It is further commented that an abbreviated condom 10 in accordance with the principles relating to the present invention is bilaterally symmetric and hence use of a two part mold with one part for either side, i.e. part line in central vertical plane, together with a single piece central insert for the interior is considered the best approach to manufacture known. Specifically, use of a two part mold so oriented will readily yield the clear draft desired of any mold in initial opening and removal from the insert is readily achieved with an air blast through the insert.

The foregoing is intended to provide one practiced in the art with the best known manner of making and using an embodiment in accordance with the principles relating to the present invention and is not to be interpreted as restrictive in any manner of the scope of the invention disclosed herein nor of the rights and privileges obtained by letters patent for which I claim:

1. An abbreviated condom intended to encompass the two bilateral lobes of the glans penis in the prevention of fluid transmission during coitus but leaving the shaft of a penis largely uncovered during use for greater sensitivity, said abbreviated condom comprising:

a bilaterally symmetric thin walled sheath possessing a closed forward end, an opposed circumferential open rear edge, a seminal fluid reservoir, a substantially continuous uninterrupted interior surface of appropriate size and shape to fit snugly about the glans penis, further possessing two bilaterally outwardly convex portions adapted to conform anatomically to both two lobes of a glans penis;

said seminal fluid reservoir possessing communication with said interior surface adjacent to said closed forward end and capable of retaining all seminal fluid resulting from an ejaculation;

whereby cohesion between said interior surface of said bilaterally symmetric outwardly convex portions and the two bilaterally symmetric lobes of the glans penis effected by anatomical conformance retains said abbreviated condom upon a glans penis during coitus and the seminal fluid resulting from ejaculation is retained in said seminal fluid reservoir.

2. The abbreviated condom of claim 1 wherein circumferential open rear edge comprises a margin with increased wall thickness and is a sufficient distance from said closed forward end to permit covering of the entire glans penis.

3. The abbreviated condom of claim 2 wherein said margin is reversible between two positions, one folded forward about the adjacent exterior surface of the abbreviated condom prior to use and a second flipped rearward behind the corona of the glans penis.

4. The abbreviated condom of claim 1 further possessing a plurality of vacuum cups molded into said interior surface of said bilaterally symmetric convex portions.

5. The abbreviated condom of claim 4 wherein said plurality of vacuum cups molded into said interior surface further cover a circumferential area.

6. The abbreviated condom of claim 4 further possessing a viscous layer upon said interior surface.

7. The abbreviated condom of claim 1 wherein said seminal fluid reservoir is located upon said closed forward end.

8. The abbreviated condom of claim 7 wherein said seminal fluid reservoir is of an accordion type construction.

9. The abbreviated condom of claim 1 wherein said seminal fluid reservoir is located between and behind said bilaterally symmetric convex portions.

10. The abbreviated condom of claim 9 further possessing an interiorly open channel facilitating communication between the interior surface of said closed forward end and said seminal fluid reservoir.

11. The abbreviated condom of claim 9 wherein said seminal fluid reservoir is comprised of an area of said thin walled sheath possessing a relatively thin thickness relative to other portions of said sheath.

12. The abbreviated condom of claim 1 manufactured with an injection molding process.

13. The abbreviated condom of claim 12 manufactured with use of a two part mold exteriorly and a single insert interiorly.

14. The abbreviated condom of claim 12 made of a polymer.

15. The abbreviated condom of claim 1 further possessing a layer of adhesive disposed upon said interior surface.

16. The abbreviated condom of claim 15 further possessing a thin film backing covering said layer of adhesive upon said interior surface.

17. The abbreviated condom of claim 15 wherein said layer of adhesive disposed upon said interior surface comprises a circumferential band.

18. The abbreviated condom of claim 15 wherein said layer of adhesive disposed upon said interior surface comprises a circumferential band located adjacent said rear circumferential rear open edge.

19. An abbreviated condom in accordance with claim 1 possessing an interior layer of resin softened by exposure to radiation.

20. An abbreviated condom in accordance with claim 19 wherein said resin is softened by exposure to ultraviolet (UV) radiation.

* * * * *